United States Patent
Hao et al.

(10) Patent No.: US 11,117,906 B2
(45) Date of Patent: *Sep. 14, 2021

(54) METHODS FOR SYNTHESIZING ZINC-LYSINE-CHLORIDE COMPLEX

(71) Applicant: Colgate-Palmolive Company, New York, NY (US)

(72) Inventors: Zhigang Hao, Bridgewater, NJ (US); Chi-Yuan Cheng, Hillsborough, NJ (US); Tatiana Brinzari, Piscataway, NJ (US); Long Pan, Somerset, NJ (US); Ravi Subramanyam, Belle Mead, NJ (US); Lauren Evans, Highland Park, NJ (US); Sergio Leite, Monmouth Junction, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/714,903

(22) Filed: Dec. 16, 2019

(65) Prior Publication Data

US 2020/0199157 A1 Jun. 25, 2020

Related U.S. Application Data

(60) Provisional application No. 62/783,694, filed on Dec. 21, 2018.

(51) Int. Cl.
| | |
|---|---|
| C07F 3/06 | (2006.01) |
| A61K 8/27 | (2006.01) |
| A61K 8/44 | (2006.01) |
| C07C 229/26 | (2006.01) |

(52) U.S. Cl.
CPC .......... *C07F 3/06* (2013.01); *A61K 8/27* (2013.01); *A61K 8/44* (2013.01); *C07C 229/26* (2013.01)

(58) Field of Classification Search
CPC combination set(s) only.
See application file for complete search history.

(56) References Cited

U.S. PATENT DOCUMENTS

| | | | |
|---|---|---|---|
| 3,941,818 A | 3/1976 | Abdel-Monem | |
| 5,061,815 A | 10/1991 | Leu | |
| 8,652,495 B2 | 2/2014 | Porter et al. | |
| 9,498,421 B2 | 11/2016 | Liu et al. | |
| 9,504,858 B2 | 11/2016 | Yuan et al. | |
| 9,532,932 B2 | 1/2017 | Prencipe et al. | |
| 9,572,756 B2 | 2/2017 | Liu et al. | |
| 9,675,823 B2 | 6/2017 | Liu et al. | |
| 9,718,843 B2 | 8/2017 | Fitzgerald et al. | |
| 9,750,670 B2 | 9/2017 | Pan et al. | |
| 9,757,316 B2 | 9/2017 | Pan et al. | |
| 9,763,865 B2 | 9/2017 | Pan et al. | |
| 9,775,792 B2 | 10/2017 | Liu et al. | |
| 9,827,177 B2 | 11/2017 | Yuan et al. | |
| 9,861,563 B2 | 1/2018 | Kilpatrick-Liverman et al. | |
| 9,883,995 B2 | 2/2018 | Prencipe et al. | |
| 9,901,523 B2 | 2/2018 | Xu et al. | |
| 9,913,784 B2 | 3/2018 | Szewczyk et al. | |
| 9,925,130 B2 | 3/2018 | Pan et al. | |
| 9,943,473 B2 | 4/2018 | Pan et al. | |
| 9,980,890 B2 | 5/2018 | Pan et al. | |
| 9,993,407 B2 | 6/2018 | Liu et al. | |
| 10,105,303 B2 | 10/2018 | Pan et al. | |
| 10,130,571 B2 | 11/2018 | Szewczyk et al. | |
| 10,188,112 B2 | 1/2019 | Hardy et al. | |
| 10,195,125 B2 | 2/2019 | Pan et al. | |
| 10,245,222 B2 | 4/2019 | Pan et al. | |
| 10,485,742 B2 | 11/2019 | Patel et al. | |
| 10,494,589 B2 | 12/2019 | Yuan et al. | |
| 2004/0198998 A1 | 10/2004 | Holerca et al. | |
| 2015/0306008 A1* | 10/2015 | Yuan ............... | A61K 31/555 424/54 |
| 2017/0121351 A1 | 5/2017 | Nawrocki et al. | |
| 2018/0116924 A1 | 5/2018 | Prencipe et al. | |
| 2018/0243193 A1 | 8/2018 | Pan et al. | |
| 2018/0256468 A1 | 9/2018 | Liu et al. | |
| 2019/0015310 A1 | 1/2019 | Pan et al. | |
| 2019/0091117 A1 | 3/2019 | Szewczyk et al. | |
| 2019/0104741 A1 | 4/2019 | Hardy et al. | |
| 2019/0117536 A1 | 4/2019 | Pan et al. | |
| 2019/0169034 A1 | 6/2019 | Dubovoy et al. | |
| 2019/0175478 A1 | 6/2019 | Szewczyk et al. | |
| 2019/0183766 A1 | 6/2019 | Pan et al. | |

FOREIGN PATENT DOCUMENTS

| | | | |
|---|---|---|---|
| EP | 0108937 | 9/1984 | |
| EP | 1529775 | 5/2005 | |
| GB | 2052978 | 2/1981 | |
| WO | WO-2014098822 A1 * | 6/2014 | ............ A61K 8/21 |

OTHER PUBLICATIONS

Google Search—smaller particles react faster_Jun. 26, 2020 (Year: 2020).*
Z. Wang, et al. A Facile Approach for the Preparation of Nano-size Zinc Oxide in Water/Glycerol with Extremely Concentrated Zinc Sources (Nanoscale Res. Lett. 2018; 13: 202, 1-9; published online Jul. 9, 2018) (Year: 2018).*
"Reaction Rates" (Downloaded Jun. 26, 2020 from: https://chem.fsu.edu/chemlab/chm1046course/rates.html; dated Feb. 1, 2001). (Year: 2001).*
Hartwell et al., 1970, "Preparation and Characterization of Tyrosine and Lysine Metal Chelate Polyesters and 3olyamides," Journal of the American Chemical Society 92(5):1284-1289.
International Search Report and Written Opinion of the International Searching Authority in International Application No. PCT/US2012/070498, dated Sep. 4, 2013.

(Continued)

Primary Examiner — Michael P Cohen (57) ABSTRACT

Disclosed herein are improved methods for the synthesis of zinc-amino acid-halide complexes via reaction of zinc oxide and amino acid hydrochloride in a solvent comprising a polyol, as well as oral care compositions comprising said complexes made according to said method.

12 Claims, 2 Drawing Sheets

(56) References Cited

OTHER PUBLICATIONS

International Search Report and Written Opinion of the International Searching Authority in International Application No. PCT/US2012/070525, dated Sep. 27, 2013.
International Search Report and Written Opinion of the International Searching Authority in International Application No. PCT/US2014/042947, dated Aug. 22, 2014.
International Search Report and Written Opinion of the International Searching Authority in International Application No. PCT/US2014/042948, dated Aug. 26, 2014.

* cited by examiner

METHODS FOR SYNTHESIZING ZINC-LYSINE-CHLORIDE COMPLEX

CROSS-REFERENCE TO RELATED APPLICATIONS

This application is a U.S. national application filed under 35 U.S.C. § 119(a) claiming priority to and the benefit of U.S. Provisional Application No. 62/783,694, filed on Dec. 21, 2018, the contents of which are hereby incorporated by reference in its entirety.

BACKGROUND

Oral cavity bacteria are the primary cause of dental ailments, including caries, gingivitis, periodontitis, and halitosis. Oral bacteria form biofilms which are tightly adhered to the oral surfaces, especially the tooth enamel. With time, these biofilms calcify and turn into tartar, making them more difficult to remove from the tooth surface. Current at-home dental treatments, such as tooth brushing and mouth rinsing, can provide only limited benefit in preventing the growth of oral biofilm, or preventing the conversion of biofilm to plaque and tartar. The only effective way to remove plaque and tartar once it has formed is through costly, sometimes uncomfortable professional dental treatments such as root planning and scaling. It would be extremely beneficial to develop means of preventing the initial formation of oral bacterial biofilms and inhibiting the growth of oral cavity bacteria. Zinc salts such as zinc oxide, zinc citrate, and zinc gluconate, have been used in the art for their antibacterial effects, but they can sometimes present difficulties in formulating oral care compositions, or they can sometimes result in undesirable taste or mouthfeel.

Complexes between metal ions and amino acids are known. Some of these, especially complexes between divalent metal ions and basic amino acids, have seen use in the field of oral care for their ability to treat dentinal hypersensitivity. Certain complexes, such as zinc-bis(lysine)-halide and zinc-bis(arginine)-halide, have been discovered to form stable, homogenous aqueous solutions, which under certain conditions, can precipitate zinc hydroxide, zinc oxide and other zinc species. The formation of such species as zinc oxide and zinc hydroxide provides a means of delivering bioactive zinc to the tissues of the oral cavity. In addition, the precipitation of these salts has enabled oral care compositions comprising these complexes to effectively plug the dentinal tubules of the teeth that transmit sensations of hypersensitivity.

These stable, soluble zinc-amino acid-halide complexes have also been disclosed as effective oral anti-bacterial agents. When placed in oral care formulations, these complexes provide an effective concentration of zinc ions to the enamel, thereby protecting against erosion, reducing bacterial colonization and biofilm development, and providing enhanced shine to the teeth. These formulations have the added benefit that they do not exhibit the poor taste and mouthfeel, poor fluoride delivery, and poor foaming and cleaning associated with conventional zinc-based oral care products using soluble zinc salts.

Of particular interest are compositions comprising the zinc-amino acid-halide complex zinc-lysine-chloride complex, designated ZLC, which may be formed, for example, by reaction of zinc oxide and lysine hydrochloride in water. ZLC has the chemical structure $[Zn(C_6H_{14}N_2O_2)_2Cl]^+Cl^-$, and may exist in solution of the cationic cation ($[Zn(C_6H_{14}N_2O_2)_2Cl]^+$) and the chloride anion, or may be a solid salt, e.g., a crystal, optionally in dihydrate form. Zinc lysine complex may also exist in a halide free complex, for example, $[Zn(C_6H_{14}N_2O_2)_2]^{2+}$. Zinc amino acid halide complexes, including zinc-lysine-chloride complexes, have been disclosed, e.g., in US 2015-0328118A1, US 2015-0335554A1, US 2015-0328110A1, and US 2015-0335553A1, the contents of each of which are hereby incorporated by reference in their entireties.

Complexes comprising zinc and amino acid and optionally an anion and/or oxygen, forms a soluble cationic moiety, which in turn may form a salt with a halide or other anion. When placed in formulation, this complex provides an effective concentration of zinc ions to the enamel, thereby protecting against erosion, reducing bacterial colonization and biofilm development, and providing enhanced shine to the teeth. Moreover, upon use, the formulation provides a precipitate that can plug the dentinal tubules, thereby reducing the sensitivity of the teeth. While providing efficient delivery of zinc in comparison to formulations with insoluble zinc salts, the formulations comprising the zinc-amino acid complex do not exhibit the poor taste and mouthfeel, poor fluoride delivery, and poor foaming and cleaning associated with conventional zinc-based oral care products using soluble zinc salts. While oral care compositions comprising zinc-amino acid-halide complexes such as the ZLC complex are known, it has been challenging to develop efficient and reliable methods of manufacturing the ZLC complex.

While the prior art discloses the use of various means of synthesizing zinc-lysine-halide complexes, such as the ZLC complex, there is still a need for additional methods which provide improved ease, efficiency and/or yield.

SUMMARY

It has now been discovered that zinc-amino acid-halide complexes, such as the ZLC complex ($[Zn(C_6H_{14}N_2O_2)_2Cl]^+C^-$) can form in improved yield by reacting zinc oxide with an amino acid hydrohalide in a solvent comprising a polyol (e.g., glycerol). In some embodiments, the solvent is substantially anhydrous. In some embodiments, the molar ratio of zinc oxide to amino acid hydrohalide is about 1:1 to about 1:3, or about 1:2.

The invention further provides oral care compositions, for example mouthwash, oral gel or dentifrice compositions, that comprise the zinc-amino acid-halide complex made according to the present synthetic methods.

The invention further provides methods of using the compositions of the invention to reduce and inhibit acid erosion of the enamel, clean the teeth, reduce bacterially-generated biofilm and plaque, reduce gingivitis, inhibit tooth decay and formation of cavities, and reduce dentinal hypersensitivity, comprising applying a composition of the invention to the teeth.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

The invention therefore provides, in a first embodiment, method of making a zinc-amino acid-halide complex (Method 1), comprising the step of reacting zinc oxide with an amino acid hydrohalide in a solvent comprising a polyol. In further embodiments of Method 1, the present disclosure provides:

1.1. Method 1 wherein the amino acid is selected from lysine, glycine and arginine, in hydrohalide acid addition salt form, e.g., hydrochloride form.

1.2. Method 1 or 1.1 wherein the amino acid is lysine or arginine.

1.3. Method 1.2, wherein the amino acid is lysine.

1.4. Any of methods 1.1 to 1.3, wherein the amino acid is in hydrochloride salt form.

1.5. Method 1, or any of 1.1 to 1.4, wherein the zinc-amino acid-halide complex has the formula $Zn(AA)_2(Hal)_2$ or $Zn(AA)_3(Hal)_2$, wherein "AA" is the amino acid and "Hal" is the halide.

1.6. Method 1.5, wherein the amino acid ("AA") is lysine, glycine or arginine.

1.7. Method 1.5 or 1.6, wherein the halide ("Hal") is chloride.

1.8. Method 1, or any of 1.1 to 1.4, wherein the zinc-amino acid-halide complex has the formula $Zn(Lys)_2Cl_2$.

1.9. Method 1.8, wherein the zinc-amino acid-halide complex has the structural formula $[Zn(C_6H_{14}N_2O_2)_2Cl]^+$ $Cl^-$, optionally in the form of a mono-hydrate or di-hydrate (e.g., $[Zn(C_6H_{14}N_2O_2)_2Cl]^+Cl^-\text{—}H_2O$).

1.10. Method 1.9, wherein the zinc-amino acid-halide complex has a structure wherein the Zn cation is coordinated by two lysine ligands with two nitrogen atoms from alpha $NH_2$ groups of the two lysine ligands and two oxygen atoms from carboxylic groups of the two lysine ligands in an equatorial plane, having a distorted square-pyramidal geometry with the apical position occupied by a chlorine atom, to form a positive cation moiety, with which a chloride anion is combined to form an ionic salt.

1.11. Method 1, or any of 1.1-1.10, wherein solvent comprises water, e.g., from 0-50% water w/w.

1.12. Method 1.11, wherein the solvent comprises from 1-30% water w/w, e.g., from 5-30% or from 10-30% w/w.

1.13. Method 1 or any of 1.1-1.10, wherein the solvent is substantially anhydrous, e.g., the solvent contains less than or equal to 1% water w/v.

1.14. Method 1.13, wherein the solvent comprises less than 0.5% water w/v, or less than 0.1% water w/v, or less than 0.05% water w/v.

1.15. Method 1 or any of 1.1-1.14, wherein the polyol is selected from one or more of a diol, a trial or a tetraol.

1.16. Method 1.15, wherein the polyol is selected from one or more of ethylene glycol, 1,2-propylene glycol, 1,3-propylene glycol, cyclopentane-1,2-diol, cyclohexane-1,2-diol, neopentyl glycol, glycerol, 1,2-butanediol, 1,3-butanediol, 1,4-butanediol, 1,5-pentanediol, and pentaerythritol.

1.17. Method 1.16, wherein the polyol is selected from one or more of ethylene glycol, 1,2-propylene glycol, 1,3-propylene glycol and glycerol.

1.18. Method 1.17, wherein the polyol is glycerol.

1.19. Method 1, or any of 1.1-1.18, wherein the solvent further comprises an alcohol, e.g., methanol, ethanol, propanol, isopropanol, or butanol.

1.20. Method 1, or any of 1.1-1.19, wherein the solvent consists essentially of glycerol (e.g., the solvent is at least 98% w/w glycerol, or at least 99% w/w glycerol, or at least 99.5% w/w glycerol).

1.21. Method 1, or any of 1.1-1.19, wherein the reaction step of reacting zinc oxide with amino acid hydrohalide occurs by combining only zinc oxide, amino acid hydrohalide and glycerol in a suitable reaction vessel.

1.22. Method 1, or any of 1.1 to 1.21, wherein the reaction step takes place at 30° C. to 200° C., e.g., at 50° C. to 180° C., or at 70° C. to 150° C., or at 100° C. to 150° C., or at 50° C. to 100° C., or at 50° C. to 75° C., or at about 60° C. or at about 120° C.

1.23. Method 1, or any of 1.1 to 1.22, wherein the method further comprises the step of removing the solvent, e.g., by distillation, vacuum distillation, evaporation, freeze-drying, or spray drying.

1.24. Method 1, or any of 1.1 to 1.23, wherein the method further comprises the step of isolating the zinc-amino acid-halide complex, e.g., in solid form and/or in substantially pure form.

1.25. Method 1.24, wherein the isolation step is by precipitation or crystallization.

1.26. Method 1.25, wherein the precipitation or crystallization step comprises the step of adding a suitable solvent to the zinc oxide/amino acid hydrohalide/solvent reaction mixture to precipitate or crystallize out the zinc-amino acid-halide complex (e.g., wherein the suitable solvent is one in which the zinc-amino acid-halide complex is poorly soluble or not soluble).

1.27. Method 1, or any of 1.1 to 1.22, wherein the method does not comprise further purification or isolation of the zinc-amino acid-halide complex, e.g., the complex is further used as the solution of the zinc-amino acid-halide complex in the solvent comprising a polyol.

1.28. Method 1, or any of 1.1 to 1.27, wherein the reaction is substantially complete (e.g., greater than 90% conversion) after less than 24 hours.

1.29. Method 1.28, wherein the reaction is substantially complete (e.g., greater than 90% conversion) after less than 12 hours or less than 6 hours or less than 4 hours or less than 3 hours, or less than 1 hour, e.g., 1 to 12 hours or 0.5 to 4 hours, or 0.1 to 1 hour.

1.30. Method 1 or any of 1.1 to 1.29, wherein the zinc oxide and the amino acid hydrohalide are combined at a molar ratio of 3:1 to 1:3, e.g., 1:1 to 1:2.5 or 1:1.5 to 1:2.5, or about 1:2.

1.31. Method 1 or any of 1.1 to 1.30, wherein the reaction mixture does not comprise an acid, e.g., does not comprise an aqueous acid.

1.32. Method 1 or any of 1.1 to 1.31, wherein the reaction mixture has a pH of from 6 to 10, e.g., from 6.5 to 10, or 6.5 to 9, or 6.5 to 8, or 7 to 10, or 7 to 9, or 7 to 8.

1.33. A zinc-amino acid-halide complex made according to Method 1 or any of Methods 1.1 to 1.32.

According to the present invention, it has been unexpectedly found that the rate of the reaction between zinc oxide and amino acid hydrohalide, and the yield of the reaction, can be significantly improved by using a polyol solvent, for example glycerol or a glycerol-water mixture.

The invention further provides a composition (Composition 1), e.g., an oral care composition or personal care composition, comprising a zinc-amino acid-halide complex made according to Method 1 or any of methods 1.1 to 1.33. In further embodiments the invention provides:

1.1. Composition 1, wherein the composition is an oral care composition.

1.2. Composition 1.1, in the form of a toothpaste, gel, mouthwash, powder, cream, strip, or gum.

1.3. Composition 1 or any of 1.1-1.2, comprising an orally acceptable base, e.g., a mouthwash, gel, or dentifrice base.

1.4. Composition 1 or any of 1.1-1.2, wherein the composition comprises the zinc-amino acid-halide complex in an amount of 0.05 to 20% by weight of the composition, e.g., from 0.1 to 10%, or from 0.5 to 5% or from 1 to 3%.

1.5. Any of the foregoing compositions in the form of a dentifrice, wherein the dentifrice base comprises an abrasive, e.g., an effective amount of a silica abrasive, e.g., 10-30%, e.g., about 20%.

1.6. Any of the foregoing compositions further comprising an effective amount of a fluoride ion source, e.g., providing 50 to 3000 ppm fluoride.

1.7. Any of the foregoing compositions further comprising an effective amount of fluoride, e.g., wherein the fluoride is a salt selected from stannous fluoride, sodium fluoride, potassium fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, and combinations thereof.

1.8. Any of the preceding compositions comprising an effective amount of one or more alkali phosphate salts, e.g., sodium, potassium or calcium salts, e.g., selected from alkali dibasic phosphate and alkali pyrophosphate salts, e.g., alkali phosphate salts selected from sodium phosphate dibasic, potassium phosphate dibasic, dicalcium phosphate dihydrate, calcium pyrophosphate, tetrasodium pyrophosphate, tetrapotassium pyrophosphate, sodium tripolyphosphate, and mixtures of any of two or more of these, e.g., in an amount of 1-20%, e.g., 2-8%, e.g., ca. 5%, by weight of the composition.

1.9. Any of the foregoing compositions comprising buffering agents, e.g., sodium phosphate buffer (e.g., sodium phosphate monobasic and disodium phosphate).

1.10. Any of the foregoing compositions comprising a humectant, e.g., selected from glycerin, sorbitol, propylene glycol, polyethylene glycol, xylitol, and mixtures thereof, e.g. comprising at least 20%, e.g., 20-40%, e.g., 25-35% glycerin.

1.11. Any of the foregoing compositions comprising one or more surfactants, e.g., selected from anionic, cationic, zwitterionic, and nonionic surfactants, and mixtures thereof, e.g., comprising an anionic surfactant, e.g., a surfactant selected from sodium lauryl sulfate, sodium ether lauryl sulfate, and mixtures thereof, e.g. in an amount of from about 0.3% to about 4.5% by weight, e.g. 1-2% sodium lauryl sulfate (SLS); and/or a zwitterionic surfactant, for example a betaine surfactant, for example cocamidopropylbetaine, e.g. in an amount of from about 0.1% to about 4.5% by weight, e.g. 0.5-2% cocamidopropylbetaine.

1.12. Any of the preceding compositions further comprising a viscosity modifying amount of one or more polysaccharide gums, for example xanthan gum or carrageenan, silica thickener, and combinations thereof.

1.13. Any of the preceding compositions further comprising flavoring, fragrance and/or coloring.

1.14. Any of the foregoing compositions comprising an effective amount of one or more antibacterial agents, for example comprising an antibacterial agent selected from halogenated diphenyl ether (e.g. triclosan), herbal extracts and essential oils (e.g., rosemary extract, tea extract, magnolia extract, thymol, menthol, eucalyptol, geraniol, carvacrol, citral, hinokitol, catechol, methyl salicylate, epigallocatechin gallate, epigallocatechin, gallic acid, miswak extract, sea-buckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, metal ions (e.g., zinc salts, for example, zinc citrate, stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, chlorite salts; and mixtures of any of the foregoing; e.g., comprising triclosan or cetylpyridinium chloride.

1.15. Any of the preceding compositions further comprising a whitening agent, e.g., a selected from the group consisting of peroxides, metal chlorites, perborates, percarbonates, peroxyacids, hypochlorites, and combinations thereof.

1.16. Any of the preceding compositions further comprising hydrogen peroxide or a hydrogen peroxide source, e.g., urea peroxide or a peroxide salt or complex (e.g., such as peroxyphosphate, peroxycarbonate, perborate, peroxysilicate, or persulphate salts; for example calcium peroxyphosphate, sodium perborate, sodium carbonate peroxide, sodium peroxyphosphate, and potassium persulfate);

1.17. Any of the preceding compositions further comprising an agent that interferes with or prevents bacterial attachment, e.g., solbrol or chitosan.

1.18. Any of the preceding compositions further comprising a source of calcium and phosphate selected from (i) calcium-glass complexes, e.g., calcium sodium phosphosilicates, and (ii) calcium-protein complexes, e.g., casein phosphopeptide-amorphous calcium phosphate 1.19. Any of the preceding compositions further comprising a soluble calcium salt, e.g., selected from calcium sulfate, calcium chloride, calcium nitrate, calcium acetate, calcium lactate, and combinations thereof.

1.20. Any of the preceding compositions further comprising a physiologically or orally acceptable potassium salt, e.g., potassium nitrate or potassium chloride, in an amount effective to reduce dentinal sensitivity.

1.21. Any of the foregoing compositions further comprising an anionic polymer, e.g., a synthetic anionic polymeric polycarboxylate, e.g., wherein the anionic polymer is selected from 1:4 to 4:1 copolymers of maleic anhydride or acid with another polymerizable ethylenically unsaturated monomer; e.g., wherein the anionic polymer is a methyl vinyl ether/maleic anhydride (PVM/MA) copolymer having an average molecular weight (M.W.) of about 30,000 to about 1,000,000, e.g. about 300,000 to about 800,000, e.g., wherein the anionic polymer is about 1-5%, e.g., about 2%, of the weight of the composition.

1.22. Any of the foregoing compositions, wherein the pH of the composition is approximately neutral, e.g., from pH 6 to pH 8 e.g., about pH 7.

1.23. Any of the forgoing compositions for use to reduce and inhibit acid erosion of the enamel, clean the teeth, reduce bacterially-generated biofilm and plaque, reduce gingivitis, inhibit tooth decay and formation of cavities, and reduce dentinal hypersensitivity.

The present disclosure further provides a method of using Composition 1, et seq., to reduce and inhibit acid erosion of the enamel, clean the teeth, reduce bacterially-generated biofilm and plaque, reduce gingivitis, inhibit tooth decay and formation of cavities, and/or reduce dentinal hypersensitivity, the method comprising applying an effective amount of a composition of the invention, e.g., any of Composition 1, et seq. to the teeth, and optionally then rinsing with water or aqueous solution sufficient to trigger precipitation of zinc salts from the composition.

For example, in various embodiments, the invention provides a method to (i) reduce hypersensitivity of the teeth, (ii) reduce plaque accumulation, (iii) reduce or inhibit demineralization and promote remineralization of the teeth, (iv) inhibit microbial biofilm formation in the oral cavity, (v) reduce or inhibit gingivitis, (vi) promote healing of sores or cuts in the mouth, (vii) reduce levels of acid producing bacteria, (viii) increase relative levels of non-cariogenic and/or non-plaque forming bacteria, (ix) reduce or inhibit formation of dental caries, (x), reduce, repair or inhibit pre-carious lesions of the enamel, e.g., as detected by quantitative light-induced fluorescence (QLF) or electrical caries measurement (ECM), (xi) treat, relieve or reduce dry mouth, (xii) clean the teeth and oral cavity, (xiii) reduce erosion, (xiv) whiten teeth, (xv) reduce tartar build-up, and/or (xvi) promote systemic health, including cardiovascular health, comprising applying any of Compositions 1, et seq. as described above to the oral cavity of a person in need thereof, e.g., one or more times per day. The invention further provides Compositions 1, et seq. for use in any of these compositions.

Without intending to be bound by theory, it is believed that the formation of the zinc amino acid halide proceeds via formation of the zinc halide then coordination of amino acid residues around a central zinc. For example, using reaction of zinc oxide with lysine hydrochloride in water as an example, the zinc can react with lysine and/or lysine HCl to form a clear solution of Zn-lysine-chloride complex ($ZnLys_3Cl_2$), wherein $Zn^{++}$ is located in an octahedral center coordinated with two oxygen and two nitrogen atoms in the equatorial plane coming from two lysine's carboxylic acids and amine groups respectively. The zinc is also coordinated to the third lysine via its nitrogen and carboxylic oxygen, at the apical position of the metal geometry.

In another embodiment, a zinc cation is complexes with two amino acid residues and two chloride residues. For example, where the amino acid is lysine, the complex has the formula $[Zn(C_6H_{14}N_2O_2)_2Cl]^+Cl^-$. In this complex, Zn cation is coordinated by two lysine ligands with two N atoms from $NH_2$ groups and O atoms from carboxylic groups in an equatorial plane. It displays a distorted square-pyramidal geometry with the apical position occupied by a $Cl^-$ atom. This novel structure gives rise to a positive cation moiety, to which a $Cl^-$ anion is combined to form an ionic salt.

Other complexes of zinc and amino acid are possible, and the precise form is dependent in part on the molar ratios of the precursor compounds, e.g., if there is limited halide, halide-free complexes may form, e.g. $ZnOLys_2$, having a pyramid geometry, with the equatorial plane that is same as the above compound (Zn is bound to two oxygen and two nitrogen atoms from different lysines), wherein the top of the pyramid is occupied by an O atom. Thus, in some embodiments, Method 1 et seq. may result in mixtures of different soluble zinc complexes, some with and some without halide as a part of the complex.

Mixtures of complexes and/or additional complex structures, e.g., involving multiple zinc ions based on the zinc structure, are possible and contemplated within the scope of the invention. When the complexes are in solid form, they may form crystals, e.g. in hydrated form.

Irrespective of the precise structure of the complex or complexes, however, the interaction of the zinc and the amino acid converts insoluble zinc oxide or zinc salts to a highly soluble complex at approximately neutral pH. With increasing dilution in water, however, the complex disassociates, and the zinc ion converts to insoluble zinc oxide. This dynamic is unexpected—typically ionic compositions become more soluble at higher dilution, not less—and this facilitates deposition of the zinc precipitate on the teeth upon administration, in the presence of saliva and with rinsing. This precipitation occludes the dentinal tubules, thereby reducing hypersensitivity, and also provides zinc to the enamel, which reduces acid erosion, biofilm and plaque formation.

It will be understood that other amino acids can be used in place of lysine in the foregoing scheme. It will also be understood that, although the zinc, amino acid and optionally halide may be primarily in the form of precursor materials or in the form of an ionic complex, there may be some degree of equilibrium, so that the proportion of material which is actually in complex compared to the proportion in precursor form may vary depending on the precise conditions of formulation, concentration of materials, pH, presence or absence of water, presence or absence of other charged molecules, and so forth.

The rate of precipitation from the formulation can be modulated by adjusting concentration of the complex in the stock solution, and changing the ratio of the stock to water. A more diluted formula leads to faster precipitation and is thus preferred when a fast treatment is desired.

As used herein, the terms "polyol," "tetraol," "triol," and "diol" refers to organic compounds bearing, respectively, at least two hydroxy groups, four hydroxy groups, three hydroxy groups, or two hydroxy groups, wherein said hydroxy groups are bound to aliphatic carbon atoms (i.e., not aromatic carbon atoms). These terms do not embrace compounds having any other functional groups. Thus, polyols, tetraols, triols and diols, as used herein, can be generally described as compounds having a formula $C_nH_m(OH)_y$, wherein y is at least two. These terms include cyclic and polycyclic compounds (e.g., cycloalkane polyols), but not phenols or other aromatic compounds. In some embodiments, polyols are C2-10 alkane polyols and/or C2-10 cycloalkane polyols.

As used herein, the term "alcohol" excludes polyols. As such, "alcohol" refers to organic compounds bearing a single aliphatic hydroxy group without any other functional groups. In some embodiments, alcohol refers to compounds having a formula $C_nH_m(OH)_y$, wherein y is 1. This term includes cyclic and polycyclic compounds (e.g., cycloalkanols), but not phenols or other aromatic compounds. In some embodiments, alcohols are C1-10 alkanols and/or C1-10 cycloalkanols.

The benefits of the oral care compositions of the invention are numerous. By providing zinc ions and zinc containing compounds that can release zinc ions in oral cavities, the oral care compositions of the invention provide antimicrobial, antiplaque, antigingivitis, anti-malodor, anticaries, and anticalculus benefits. The occluding particles and the surface deposits are compounds containing zinc (particularly ZnO), as well as other zinc derivatives which can release zinc ions into oral cavities and provide the various benefits as recognized above. Additional benefits include but are not limited to anti-attachment, anti-periodontitis and anti-bone loss, as well as promotion of wound healing.

A second benefit is the antierosive properties of zinc ions, which form antierosive deposits on tooth surfaces through oxidation and hydrolysis. The surface deposits, as well as the occluding particles, can react with and neutralize acids, thus protecting the dental surface from the erosive effects of the acids. In this regard, the more surface depositions/occlusion the treatments lead to, the more efficacious the treatments are, and therefore zinc-arginine and zinc-lysine are preferred. It is also noted that when the surface deposits and occluding particles neutralize acids, beneficial zinc ions and amino acids (infra) can be released, providing oral care benefits other than anti-erosion.

A third benefit is anti-sensitivity benefit as a result of the occlusion. Occlusion of dentin tubules leads to sensitivity relief.

A fourth benefit is the benefit associated with amino acids. The occluding particles and surface deposits contain the corresponding amino acids, such as arginine and lysine. These amino acids provide multiple benefits. For example, basic amino acids lead to higher pH of the plaque and can provide anticaries benefits.

Examples of amino acids include, but are not limited to, the common natural amino acids, e.g.: lysine, arginine, histidine, glycine, serine, threonine, asparagine, glutamine, cysteine, selenocysteine, proline, alanine, valine, isoleucine, leucine, methionine, phenylalanine, tyrosine, tryptophan, aspartic acid, and glutamic acid. In some embodiments the amino acid is a neutral or acidic amino acid, e.g., glycine.

The halide may be chlorine, bromine, or iodine, most typically chlorine. The acid addition salt of an amino acid and a halogen acid (e.g., HCl, HBr, or HI) is sometimes referred to herein as an amino acid hydrohalide. Thus one example of an amino acid hydrohalide is lysine hydrochloride. Another is glycine hydrochloride.

In certain embodiments, compositions according to the present disclosure may be anhydrous. By anhydrous, there is less than 5% by weight water, optionally less than 4, less than 3, less than 2, less than 1, less than 0.5, less than 0.1 down to 0% by weight water. Especially in such compositions, the zinc-amino acid-halide complex may be added to the composition as a solution in glycerol, e.g., a concentrated solution in glycerol.

Unless stated otherwise, all percentages of composition components given in this specification are by weight based on a total composition or formulation weight of 100%.

The compositions and formulations as provided herein are described and claimed with reference to their ingredients, as is usual in the art. As would be evident to one skilled in the art, the ingredients may in some instances react with one another, so that the true composition of the final formulation may not correspond exactly to the ingredients listed. Thus, it should be understood that the invention extends to the product of the combination of the listed ingredients.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

EXAMPLES

The general reaction for formation of ZLC is as follows:

$$ZnO + 2(Lysine.HCl) \rightarrow [Zn(Lysine)_2Cl]Cl(ZLC) + 2H_2O$$

An approximately 1:2 molar ratio of zinc oxide to lysine hydrochloride may be suspended or dissolved in a suitable solvent and stirred until the reactants disappear, indicating completion of the formation of the soluble ZLC complex.

Prior art methods of preparing ZLC complex by combining zinc oxide and lysine hydrochloride in aqueous solution typically required very long reaction times (e.g., 12 hours or more, 24 hours or more, or up to 3 days) for completion of the reaction. For example, WO 2015/195118 discloses a synthesis method comprising reacting a 1:2 molar ratio of zinc oxide and lysine hydrochloride in water followed by stirring at room temperature for 12 hours. WO 2015/195117 discloses a method comprising reacting a 1:2 molar ratio of zinc oxide and lysine hydrochloride in dilute aqueous hydrochloric acid (at a pH of 5-6) followed by stirring at room temperature for several hours. Such prior art methods share the additional drawback, however, that the removal of water from a reaction mixture is considerably more difficult than the removal of an organic solvent. Water has a relatively high boiling point, combined with a very high heat of vaporization, making the removal of water by thermal means very energy intensive. Furthermore, it has become common to formulate oral care compositions in the form of anhydrous compositions making it necessary to provide ZLC complex in an anhydrous form.

The present invention overcomes these difficulties by providing ZLC complex in a solvent or solvent mixture much more amenable to solvent removal or direct incorporation into oral care compositions.

Example 1: ZLC Synthesis in Anhydrous Glycerol

Synthesis: 243.5 g of L-lysine hydrochloride (1.33 mol) is added to 1000 g of glycerol (>99.5%), followed by the addition of 54.3 g of zinc oxide (0.667 mol). The mixture is stirred at 800 rpm speed at 120° C. for three hours. All solids dissolve to yield a clear, colorless solution. Based on the raw materials combined for the reaction mixture, the expected ZLC concentration in glycerol is 22% (w/w). After cooling to room temperature, an aliquot of the reaction mixture ("Sample A") is analyzed using NMR and FTIR in comparison to pure ZLC crystal dissolved in glycerol. In addition, an aliquot of the reaction mixture ("Sample A") is diluted with methanol and analyzed using liquid chromatography electrospray ionization-tandem mass spectrometry (LC-MS) methods.

Comparative Syntheses: A second preparation of ZLC complex is made by combining zinc oxide and lysine hydrochloride in distilled water (without added acid). The reaction mixture is stirred for 3 days at room temperature, at which time all of the suspended solids had dissolved. A sample of this reaction mixture is spray dried to afford a white amorphous solid. A sample ("Sample C") of this solid is dissolved in glycerol for NMR and FTIR analysis.

A sample of the white amorphous solid is then crystallized from ethanol to afford a white crystalline solid. A sample ("Sample B") of this solid is dissolved in glycerol for NMR and FTIR analysis.

LCMS Analysis: LC-MS analysis is performed using an AB Sciex tandem mass spectrometer (AB Sciex LLC, Framingham, Mass., USA) equipped with an ESI interface and Agilent 1260 capillary LC system (Model Agilent 1260, Agilent Technologies, Palo Alto, Calif., USA) with a DAD detector (G1315C) and an Agilent Zorbax SB-Aq column with 2.1 mm i.d.×50 mm dimension and 3.5 µm particle size (Agilent Technologies, Palo Alto, Calif., USA Part No. 871700-914). The mobile phase is methanol at a flow rate was 70 µL/min (injection volume 1 µL). The AB Sciex tandem mass spectrometer is operated in the positive-ion mode with nitrogen as curtain gas at 10 psi, ion source gas at 10 psi. ESI IonSpray voltage is set at 5.5 kV in ESI interface. The declustering and entrance potential are set at 80 V and 5.5 V, respectively. The temperature of the ionization interface is maintained at 550° C. For total ion count (TIC) mode, the MS screen range is from 50 to 1000 m/z.

NMR Analysis: $^{13}C$ NMR studies are performed on a Bruker Avance spectrometer (Bruker-Biospin, Billerica, Mass., USA) with a 5 mm BBI probe operating at 500.0 MHz for $^1H$ and 125.7 MHz for $^{13}C$ in glycerol at 25° C. All $^{13}C$ NMR spectra are obtained using an $^1H$ decoupling sequence ("zgig" from Bruker pulse-program library) with a repetition time of 15 sec and 8192 transients. An aliquot of the reaction mixture is directly transferred into a 5 mm NMR tube and the $^{13}C$ NMR spectrum is recorded.

FTIR Analysis: Infrared spectra are collected using a Bruker Vertex 70 FTIR spectrometer equipped with a Gladi-ATR diamond ATR accessory (Pike technologies, Madison, Wis.). The spectral range is 80-4000 $cm^{-1}$ and a resolution of 4 $cm^{-1}$ is used. All measurements are carried out at room temperature on as-prepared glycerol solutions without any additional sample preparation.

LCMS Results: The LCMS spectrum shows a single major LC peak demonstrating the typical zinc isotopic triplet cluster at 354.3, 356.3 and 358.3 m/z. This matches the MS spectrum previously obtained for the ZLC complex, the m/z 354/356/358 triplet corresponding to the Zn(lysine)$_2$ complex fragment.

Figure 1:
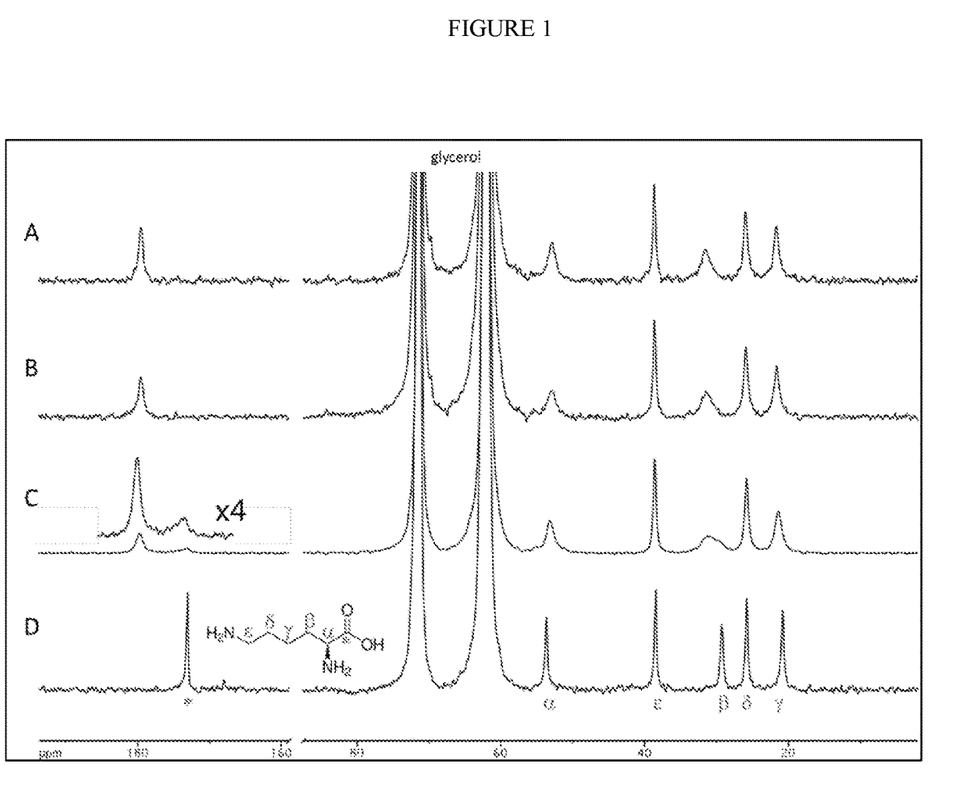
FIG. 1 shows overlaid $^{13}C$ NMR spectra comparing the ZLC product made according to the present disclosure by reacting zinc oxide and lysine hydrochloride in glycerol ("A"), in comparison to pure ZLC obtained after crystallization from ethanol ("B"), ZLC obtained by spray-drying from an aqueous reaction mixture ("C") and reference lysine-HCl standard ("D").

NMR Results: NMR results are shown in FIG. 1. The $^{13}C$-NMR spectrum of the diluted reaction sample is compared to standard spectra of L-lysine HCl in glycerol ("Sample D") as well as Samples B and C. The chemical shift of the carbonyl carbon in the experimental sample is located at 180 ppm as a single peak, which matches the peak in the Sample B and C controls, and which is different than the carbonyl carbon of the Sample D lysine standard at 173 ppm. This finding demonstrates formation of ZLC complex, and absence of unreacted lysine, in the reaction mixture according to the present invention. This finding is also consistent with the ZLC complex's structure having the lysine carboxyl groups bound to the zinc ion center.

In addition, while the crystallized ZLC Sample B spectrum also shows an absence of lysine starting material, the spray dried aqueous reaction mixture of Sample B demonstrates a weak but visible peak for unreacted lysine.

FTIR Results

Figure 2:
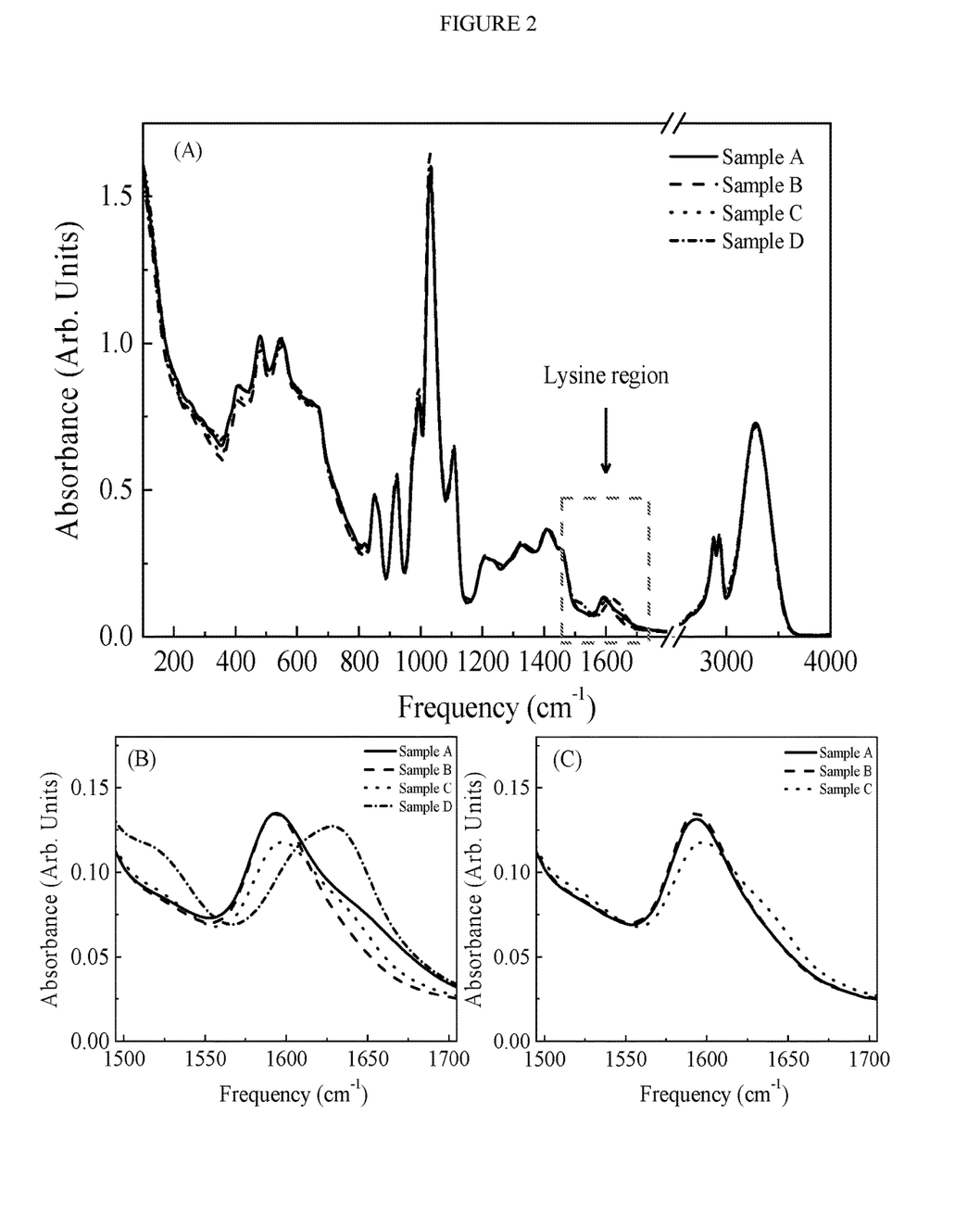
FIG. 2 shows overlaid FTIR spectra comparing the ZLC product made according to the present disclosure by reacting zinc oxide and lysine hydrochloride in glycerol ("A"), in comparison to pure ZLC obtained after crystallization from ethanol ("B"), ZLC obtained by spray-drying from an aqueous reaction mixture ("C") and reference lysine-HCl standard ("D").

FIG. 2 displays a comparison of infrared spectra for Samples A, B, C and D, as described above. FIG. 2(A) shows the full IR spectrum, while FIG. 2(B) shows a close-up view of the lysine peaks that are free of overlap from the background glycerol spectrum. The spectra demonstrate the presence of free lysine bands near 1520 $cm^{-1}$ and 1630 $cm^{-1}$ in the spray-dried ZLC Sample C, as compared to the pure ZLC crystal Sample B. In contrast, the sample prepared according to the present invention, Sample A, displays a profile that closely resembles the pure ZLC crystal (Sample B) with the exception of an extra band located near 1650 $cm^{-1}$. This latter band is attributed to the presence of water in this reaction mixture. Subtraction of the water peak, as shown in FIG. 2(C), demonstrates that Sample A's vibrational profile is substantially identical to that of the pure ZLC crystal, suggesting that this newly synthesized material has a lysine local structure that is similar to ZLC crystal.

Example 2: ZLC Synthesis in Aqueous Glycerol

The synthetic procedure of Example 1 is repeated using 210.7 g of lysine hydrochloride (1.15 mol) and 46.9 g of zinc oxide (0.576 mol) in 420 g of glycerol (333 mL) and 180 g of water (180 mL) (30% w/w water to glycerol), stirring at a temperature of 60° C. The reaction mixture quickly becomes clear and colorless. Aliquots are taken from the reaction mixture at 2, 5, 10, 20, 30, 40, 50 and 60 minutes after mixing and directly analyzed by FTIR as described in Example 1. In addition, the samples taken at 2 minutes and 60 minutes are also analyzed by NMR as described in Example 1. Further, one aliquot is taken from the reaction mixture before addition of zinc oxide (representing lysine hydrochloride in water-glycerol as a control (at time=0 min).

Samples are analyzed according to the procedures described in Example 1, except that NMR spectra are obtained at a temperature of −10° C. to slow down proton exchange.

FTIR: Comparison of the FTIR spectra at different reaction time points demonstrates that substantially all of the free lysine evident in the control spectrum is absent within 5 minutes of reaction. The FTIR spectra from the time points from 10 to 60 minutes are found to be essentially identical and lacking in (and/or having significantly reduced) major free lysine peaks at about 1520 $cm^{-1}$ and 1630 $cm^{-1}$.

NMR: Both the spectra obtained at 2 minutes and at 60 minutes show a strong peak for the zinc-complex lysine carboxyl group (180 ppm) and only a very weak peak for free lysine (173 ppm). Relative peak integrals indicate that the reaction mixture is 90.8% ZLC and 9.2% free lysine at both the 2-minute and 60-minute time points.

Further Studies: The reaction procedure and NMR analysis (2 minute time point) are repeated in parallel using 10% w/w water-glycerol, 20% w/w water-glycerol, and 32.5% w/w water-glycerol as the reaction solvent. The results show that at 10% water, the reaction is 94.1% complete at 2 minutes, while at 20% water the reaction is 93.6% complete at 2 minutes. At 32.5% water, the reaction is 90.5% complete.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the scope of the invention should be construed broadly as set forth in the appended claims.

The invention claimed is:

1. A method of making a zinc-amino acid-halide complex, comprising the step of reacting zinc oxide with an amino acid hydrohalide in a solvent comprising a polyol, wherein the amino acid is lysine and the zinc-amino acid-halide complex has the structural formula $[Zn(C_6H_{14}N_2O_2)_2Cl]^+$ $Cl^-$, and wherein the method comprises reacting zinc oxide with lysine hydrochloride at a 1:2 molar ratio in anhydrous glycerol or in glycerol with 30% w/w of water.

2. The method of claim 1, wherein the solvent is substantially anhydrous.

3. The method of claim 1, wherein the solvent further comprises one or more of ethylene glycol, 1,2-propylene glycol, 1,3-propylene glycol, cyclopentane-1,2-diol, cyclohexane-1,2-diol, neopentyl glycol, 1,2-butanediol, 1,3-butanediol, 1,4-butanediol, 1,5-pentanediol, and pentaerythritol.

4. The method of claim 1, wherein the solvent further comprises an alcohol.

5. The method of claim 1, wherein the solvent consists essentially of glycerol.

6. The method of claim 1, wherein the method further comprises the step of removing the solvent by distillation, vacuum distillation, evaporation, freeze-drying, or spray drying.

7. The method of claim 1, wherein the method further comprises the step of isolating the zinc-amino acid-halide complex in solid form and/or in substantially pure form.

8. The method of claim 7, wherein the isolation step is by precipitation or crystallization.

9. The method of claim 1, wherein the reaction is substantially complete after less than 24 hours.

10. The method of claim 9, wherein the reaction is substantially complete after less than 6 hours or less than 4 hours or less than 3 hours, or less than 1 hour.

11. A zinc-amino acid-halide complex made according to claim 1.

12. An oral care or personal care composition comprising the complex according to claim 11.

* * * * *